United States Patent [19]

Eakins et al.

[11] 4,228,176

[45] Oct. 14, 1980

[54] THROMBOXANE INHIBITION WITH BURIMAMIDE

[75] Inventors: Kenneth E. Eakins, Sparkill; Geoffrey Allan, New York, both of N.Y.

[73] Assignee: Nelson Research & Development Company, Irvine, Calif.

[21] Appl. No.: 28,544

[22] Filed: Apr. 9, 1979

Related U.S. Application Data

[62] Division of Ser. No. 903,584, May 8, 1978, Pat. No. 4,172,139.

[51] Int. Cl.$^2$ .......................................... A61K 31/415
[52] U.S. Cl. ............................................... 424/273 R
[58] Field of Search ........................................ 424/273

*Primary Examiner*—Stanley J. Friedman
*Attorney, Agent, or Firm*—Martin A. Voet

[57] ABSTRACT

The disclosure describes a method for selectively inhibiting thromboxane biosynthesis with Burimamide, a compound previously known to be a histamine $H_2$-receptor blocker. The discovery is useful in the treatment of a number of cardiovascular and inflammatory diseases in which thromboxane biosynthesis is involved.

7 Claims, No Drawings

THROMBOXANE INHIBITION WITH BURIMAMIDE

This is a division of application Ser. No. 903,584 filed May 8, 1978, now U.S. Pat. No. 4,172,139.

BACKGROUND OF THE INVENTION

1. Field of the Invention

The present invention relates to the treatment of disease conditions which are caused by or are related to the biosynthesis of thromboxane, such as inflammatory and cardiovascular diseases.

2. Background of the Prior Art

Burimamide is a compound known in the art, having the chemical structure N-methyl-N'-[4-(imidazole-4-yl)butyl] thiourea, and having the pharmacologic activity of an $H_2$-receptor blocker, see, for example, Ganellin and Owen," The Pressor Activity of Burimamide: A Relationship Between Chemical Constitution and Pressor Activity of Burimamide and Related Histamine $H_2$-Receptor Antagonists," Agents and Actions, Vol. 7/1 (1977) and cited references.

Heretofore, Burimamide was known to inhibit histamineinduced gastric acid secretion making the compound useful in treating ulcers.

Imidazole is known as a selective inhibitor of thromboxane biosynthesis, see, for example, Needleman and others, "Application of Imidazole as a Selective Inhibitor of Thromboxane Synthetase in Human Platelets," Proc. Natl. Acad. Sci. U.S.A. 74:1716–1720 (1977). Various imidazole analogues have been studied but only 1-methyl imidazole has heretofore been found to be a potent inhibitor of thromboxane biosynthesis, see Moncada and others "Imidazole: A Selective Inhibitor of Thromboxane Synthetase," Prostaglandins 13:611–618, (1977).

3. Summary of the Invention

The invention relates to the discovery that Burimamide is a potent, selective blocker of thromboxane biosynthesis and that other closely related $H_2$-receptor blockers do not have this activity. The discovery is useful in the therapeutic or prophylacetic treatment of a number of disease processes in which thromboxane is involved, including inflammatory diseases, such as, for example, psoriasis, pruritis, eczema, allergy and asthma; and cardiovascular diseases, such as, for example, stroke, heart attack, thrombus formation and platelet aggregation. Burimamide may also be used in in vitro blood platelet systems including whole blood as kept in blood banks, whole blood as used in heart-lung machines and platelet-rich concentrates.

DETAILED DESCRIPTION

For in vivo applications the compositions of the present invention are presented for administration to humans and animals in ointments, creams, gels or other conventional topical carriers for topical use, and in unit dosage forms, such as tablets, capsules, pills, powders, granules, sterile parenteral solutions or suspensions, and oil-in-water and water-in-oil emulsions containing suitable quantities of Burimamide.

For oral administration either solid or fluid unit dosage forms can be prepared. For preparing solid compositions such as tablets, a suitable compound as disclosed herein is mixed with conventional ingredients such as talc, magnesium stearate, dicalcium phosphate, magnesium aluminum silicate, calcium sulfate, starch, lactose, acacia methylcellulose, and functionally similar materials as pharmaceutical diluents or carriers. Capsules are prepared by mixing Burimamide with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing Burimamide and a sterile vehicle, water being preferred. The compound, depending on the vehicle and concentration used, can be either suspended or dissolved in the vehicle. In preparing solutions the compound can be dissolved in water for injection and filler sterilized before filling into a suitable vial or ampul and sealing.

Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For in vitro applications, both sterile and nonsterile, aqueous solutions are prepared by dissolving the compound in water and adding salt to provide an isotonic solution and buffering to a pH compatible with blood.

Advantageously the composition prepared for parenteral administration can be used when prepared omitting the local anesthetic.

The dosage for humans and animals depends on the blood volume and condition of the subject. A dosage schedule of from about 0.1 to about 100 mg per dose administered 1 to 3 times daily is effective for reducing platelet aggregation in the subject. Expressed in terms of weight, the dose can be from 0.001 to 1.5 mg/kg/day. The preferred dose is 1 to 10 mg orally 1 to 3 times a day for an adult human. For in vitro, dosage is from 0.01 to 50 micrograms/ml of whole blood.

The addition of Burimamide disclosed herein to whole blood provides in vitro applications of the invention such as in the storage of whole blood in blood banks, and whole blood to be used in heart-lung machines. Additionally, whole blood containing Burimamide can be circulated through organs, e.g., heart and kidneys, which have been removed from a cadaver and prior to transplant.

Burimamide can also be used for the preparation of stable platelet-rich plasma concentrates in the same manner as the prostaglandins as disclosed in U.S. Pat. No. 3,629,071 and Science. Vol. 175, pp. 526-542 (Feb. 4, 1972).

In vivo applications are the administration to humans and animals in the cardiovascular area of medicine to prevent clot formation in situations such as following surgery to prevent postoperative thrombosis; in geriatric patients to prevent transient cerebral ischemic attacks and long-term prophylaxis following myocardial infarcts and strokes. Burimamide may also be used topically in the treatment of inflammatory diseases such as allergy, eczema, psoriasis, pruritis and asthma.

The following examples describe the manner and process of making and using the invention and set forth the best mode contemplated by the inventor of carrying out the invention but are not to be construed as limiting.

EXAMPLE 1

| Burimamide | 0.9 | gm |
|---|---|---|
| Cetyl alcohol | 5.4 | gm |
| Stearyl alcohol | 5.4 | gm |
| Na lauryl sulfate | 1.35 | gm |
| White petrolatum | 27.0 | gm |
| Propylene glycol | 9.0 | gm |
| Distilled water q.s. | 90 | gm |

The oil phase is prepared by melting the petrolatum, cetyl and stearyl alcohols together. The remaining ingredients are dissolved in the water and added to the oil phase to form a cream.

The cream is useful in the treatment of psoriasis by rubbing on the psoriatic lesions twice a day.

EXAMPLE 2

The following topical compositions are useful in treating inflammations of the skin by application to the affected skin areas three times a day.

| OINTMENT | | |
|---|---|---|
| Burimamide | 1 | gm |
| Spermaceti | 27 | gm |
| Beeswax | 27 | gm |
| Carbapol 934 q.s. | 100 | gm |
| CREAM | | |
| Burimamide | 1 | gm |
| Polyethylene glycol 400 | 37.5 | gm |
| 1,2,6-hexanetriol | 20 | gm |
| Polyethylene glycol 4,000 q.s. | 100 | gm |
| CREAM | | |
| Burimamide | 5 | gm |
| Polyethylene glycol 400 | 37 | gm |
| Polyethylene glycol 400 monostearate | 26 | gm |
| Polyethylene glycol 4000 q.s. | 100 | gm |
| CREAM | | |
| Burimamide | 5 | gm |
| Polyethylene glycol 400 | 47.5 | gm |
| Cetyl alcohol | 5 | gm |
| Polyethylene glycol 4000 q.s. | 100 | gm |
| OINTMENT | | |
| Burimamide | 10 | gm |
| Anhydrous lanolin | 20 | gm |
| Mineral Oil | 25 | gm |
| White petrolatum q.s. | 100 | gm |

EXAMPLE 3

One thousand grams of composition are made from the following types and amounts of ingredients:

| Burimamide | 5 | gm |
|---|---|---|
| Cholesterol | 50 | gm |
| Cetyl alcohol | 60 | gm |
| Stearyl alcohol | 60 | gm |
| Spermaceti | 60 | gm |
| Stearic acid | 100 | gm |
| Glyceryl monooleate | 50 | gm |
| White petrolatum | 80 | gm |
| Squalene | 50 | gm |
| Corn oil | 185 | gm |
| Oleic acid | 200 | gm |
| Glyceryl monostearate | 100 | gm |

Melt all solids, add liquids, and heat until a clear solution results. Strain through cheesecloth and allow to cool at room temperature.

The composition so prepared is usefully applied to the human skin for treatment of eczema.

EXAMPLE 4

One thousand grams of the composition of the present invention are prepared from the following types and amounts of ingredients:

| Burimamide | 5 | gm |
|---|---|---|
| Stearic acid | 100 | gm |
| Oleic acid | 200 | gm |
| Glyceryl monooleate | 50 | gm |
| Glyceryl monostearate | 100 | gm |
| Corn oil | 245 | gm |
| Spermaceti | 20 | gm |
| Liquid petrolatum, viscosity 180 | 80 | gm |
| Squalene | 50 | gm |
| Cholesterol | 30 | gm |
| Cetyl alcohol | 40 | gm |
| Stearyl alcohol | 30 | gm |
| Lauryl alcohol | 50 | gm |

Melt all solid ingredients together, add the liquid ingredients, and heat until a clear solution results. Strain through cheesecloth and allow to cool at room temperature.

The composition so prepared is usefully applied to the human skin for treatment of pruritis.

EXAMPLE 5

One thousand grams of topical cream is prepared from the following types and amounts of ingredients:

| Burimamide | 100 | gm |
|---|---|---|
| Polysorbate 80 | 50 | gm |
| Tegacid regular* | 150 | gm |
| Spermaceti | 100 | gm |
| Propylene glycol | 50 | gm |
| Methylparaben | 1 | gm |
| Deionized water q.s. | 1,000 | gm |

*Self-emulsifying glyceryl monostearate from Goldschmidt Chemical Corporation, New York, N.Y.

The Tegacid and spermaceti are melted together at a temperature of 70°-80° C. The methylparaben is dissolved in about 500 gm of water and the propylene glycol, polysorbate 80, and Burimamide are added in turn, maintaining a temperature of 75°-80° C. The methylparaben mixture is added slowly to the Tegacid and spermaceti melt, with constant stirring. The addition is continued for at least 30 minutes with additional stirring until the temperature has dropped to 40°-45° C. Finally, sufficient water is added to bring the final weight to 1,000 gm and the preparation stirred to maintain homogeneity until cooled and concealed.

The composition is applied to human skin three times a day to treat contact dermatitis.

EXAMPLE 6

A Lot of 10,000 tablets, each containing 0.1 mg of sodium burimamide is prepared from the following types and amounts of ingredients:

| Burimamide | 1 | gm |
|---|---|---|
| Dicalcium phosphate | 1,500 | gm |
| Methylcellulose, U.S.P. (15 cps.) | 60 | gm |
| Talc | 150 | gm |
| Corn starch | 200 | gm |
| Calcium stearate | 12 | gm |

The active compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets. These tablets are useful in preventing thrombus formation at a dose of 1 tablet every four hours following surgery.

EXAMPLE 7

One thousand two-piece hard gelatin capsules, each containing 100 mg of Burimamide are prepared from the following types and amounts of ingredients:

| Burimamide | 100 | gm |
|---|---|---|
| Talc | 100 | gm |
| Magnesium stearate | 10 | gm |

These ingredients are mixed well and filled into capsules of the proper size. Capsules so prepared are useful in preventing further coronary infarcts at a dose of 1 capsules daily to a patient recovering from a coronary infarct.

EXAMPLE 8

One thousand tablets, each containing 100 mg of Burimamide are prepared from the following types and amounts of ingredients:

| Burimamide | 100 | gm |
|---|---|---|
| Microcrystalline cellulose NF | 120 | gm |
| Starch | 16 | gm |
| Magnesium stearate powder | 4 | gm |

These ingredients are screened and blended together and pressed into 240 mg tablets. The tablets are useful to protect against transient cerebral ischemic attacks at a dose of 1 tablet daily.

EXAMPLE 9

A sterile preparation suitable for intramuscular injection and consisting of 1 mg of Burimamide each milliliter is prepared from the following ingredients:

| Burimamide | 1 | gm |
|---|---|---|
| Benzyl benzoate | 200 | ml |
| Methylparaben | 1.5 | gm |
| Propylparaben | 0.5 | gm |
| Cottonseed oil, q.s. | 1,000 | ml |

One milliliter of this sterile preparation is injected for prophylactic treatment prior to surgery.

EXAMPLE 10

A comparison of the inhibition of thromboxane biosynthesis between imidazole and Burimamide was made. Tables 1 and 2 show the results of the study.

TABLE 1

Inhibition of Thromboxane Biosynthesis by Imidazole and Burimamide

| Concentration mg/ml | % Inhibition Imidazole | % Inhibition Burimamide |
|---|---|---|
| 0.5 | 0 | 15 |
| 1 | 25 | 21 |
| 2 | 53 | 36 |
| 5 | 68 | 47 |
| 10 | 81 | 58 |
| 20 | 89 | 73 |
| 50 | 88 | 86 |
| 100 | — | 98 |

EXAMPLE 11

A number of structurally related compounds including other $H_2$ blockers were compared for inhibition of thromboxane activity. Table 2 shows the results of the study.

TABLE 2

Inhibition of Thromboxane Biosynthesis (Compounds Studied at a Concentration of 100 mg/ml)

| NAME | STRUCTURE | % INHIBITION |
|---|---|---|
| Burimamide | imidazole-(CH$_2$)$_4$-NH-C(=S)-NH-CH$_3$ | 100% |
| Metiamide | 5-methylimidazole-CH$_2$-S-(CH$_2$)$_2$NH-C(=S)-NH-CH$_3$ | 33% |
| Cimetidine | 5-methylimidazole-CH$_2$-S(CH$_2$)$_2$-NH-C(=N-C≡N)-NH-CH$_3$ | 19% |

TABLE 2-continued

Inhibition of Thromboxane Biosynthesis
(Compounds Studied at a Concentration of 100 mg/ml)

| NAME | STRUCTURE | % INHIBITION |
|---|---|---|
| Histamine | 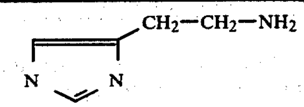 | 17% |
| 2-(2-thiazolyl) Ethylamine | 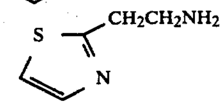 | 19% |
| 2-(2-pyridyl) Ethylamine | | 20% |
| 4-Methylhistamine | 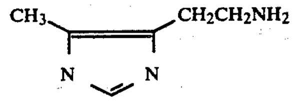 | 0% |
| Dimaprit | 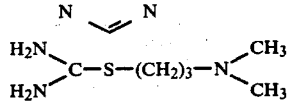 | 35% |
| N-acetyl Histamine | 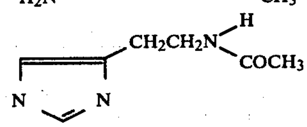 | 26% |
| N-acetyl Histidine | 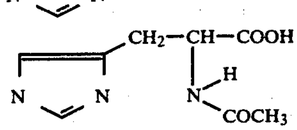 | 0% |
| L-Histidine | 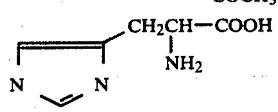 | 17% |
| Imidazole | 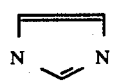 | 100% |
| Clonidine | 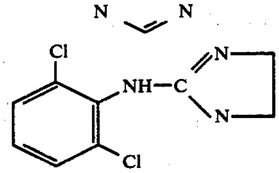 | 0% |
| Levamisole | 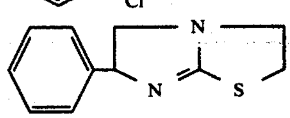 | 6% |

As is apparent, the only compound comparable in inhibition of thromboxane biosynthesis is imidazole. Furthermore, structurally similar $H_2$-receptor blocker compounds such as metiamide and cimetidine, have only minor thromboxane inhibitory activity.

We claim:

1. A method for treatment of an imflammatory disease condition comprising the administration to a human or animal suffering from an inflammatory disease condition of an effective, anti-inflammatory amount of Burimamide or a pharmaceutically acceptable salt thereof.

2. The method of claim 1 wherein the inflammatory disease is psoriasis.

3. The method of claim 1 wherein the inflammatory disease is allergy.

4. The method of claim 1 wherein the inflammatory disease is eczema.

5. The method of claim 1 wherein the inflammatory disease is pruritis.

6. The method of claim 1 wherein the inflammatory disease is inflammation of the eye.

7. The method of claim 1 wherein the inflammatory disease is asthma.

* * * * *